United States Patent [19]

Cornell et al.

[11] Patent Number: 5,670,169
[45] Date of Patent: Sep. 23, 1997

[54] WOUND HYDRATING GEL WITH NOVEL PRESERVATIVE SYSTEM AND LOW CYTOTOXICITY

[75] Inventors: Marc D. Cornell, St. Louis, Mo.;
Nancy E. Kaiser, Granite City, Ill.;
Rita A. Brenden, St. Louis, Mo.

[73] Assignee: E.R. Squibb & Sons, Inc., Princeton, N.J.

[21] Appl. No.: 170,941

[22] Filed: Dec. 20, 1993

[51] Int. Cl.$^6$ .............. A61K 9/10; A61K 47/36; A61K 47/38
[52] U.S. Cl. ............ 424/488; 252/315.3; 514/944; 524/916
[58] Field of Search ................ 424/484, 488; 252/315.3; 524/916; 514/944

[56] References Cited

U.S. PATENT DOCUMENTS

| | | | |
|---|---|---|---|
| 3,640,741 | 2/1972 | Etes | 424/401 |
| 4,391,799 | 7/1983 | Mason et al. | 424/132 |
| 4,393,048 | 7/1983 | Mason et al. | 424/132 |
| 4,470,814 | 9/1984 | Chang et al. | 523/120 |
| 4,503,034 | 3/1985 | Maupetit et al. | 424/80 |
| 4,585,650 | 4/1986 | Newberry, Jr. et al. | 424/73 |
| 4,664,105 | 5/1987 | Dautzenberg et al. | 128/156 |
| 4,745,098 | 5/1988 | Michaeli | 514/2 |
| 4,808,570 | 2/1989 | Michaeli | 514/2 |
| 4,842,866 | 6/1989 | Horder et al. | 424/485 |
| 4,948,575 | 8/1990 | Cole et al. | 424/128 |
| 5,013,769 | 5/1991 | Murray et al. | 523/111 |
| 5,192,802 | 3/1993 | Rencher | 424/426 |
| 5,271,943 | 12/1993 | Bogart et al. | 424/443 |

FOREIGN PATENT DOCUMENTS

| | | |
|---|---|---|
| 0 047 647 A2 | 3/1982 | European Pat. Off. |
| 0 532 275 A1 | 3/1993 | European Pat. Off. |
| 2 082 911 | 3/1982 | United Kingdom |
| 90/14110 | 11/1990 | WIPO |

OTHER PUBLICATIONS

WOUNDS: vol. 5, No. 3 May/Jun. 1993, Mulder et al. pp. 112–115.
Cosmetics & Toiletries, vol. 97, Nov. 1982, pp. 32, 38.
WOUNDS: Premier Issue, Apr. 1989, Alvarez et al. pp. 35–50.

*Primary Examiner*—Edward J. Webman
*Attorney, Agent, or Firm*—Theodore R. Furman, Jr.; John M. Kilcoyne

[57] ABSTRACT

The present invention relates to a preserved, yet non-cytotoxic alginate based hydrating gel system for the purpose of treating wounds that need moisture. Sodium carboxymethylcellulose and an alginate polymer blend impart sufficient viscosity to an aqueous solution to provide moisture to the wound. The blend reduces the cytotoxicity of a combination of preservatives incorporated into the system. More specifically, the invention relates to a wound hydrating gel comprising a) a hydrocolloid mixture of carboxymethylcellulose and sodium/calcium alginate, and b) a preservative system. This invention further relates to methods of preparing and using the wound hydrating gel.

16 Claims, No Drawings

WOUND HYDRATING GEL WITH NOVEL PRESERVATIVE SYSTEM AND LOW CYTOTOXICITY

BACKGROUND OF THE INVENTION

It is well known that the healing of normal wounds is significantly enhanced by providing a moist environment for the wound during healing. Material dressing design for wound repair is largely based on the control of local hydration and oxygen tension.

The ability of a dressing to transmit moisture vapor from a wound bed to the external atmosphere is referred to as occlusion. It characterizes the relative permeability of that dressing to gases. Occlusion influences both epidermal resurfacing and dermal repair.

Exposed wounds are more inflamed, painful, itchy, and have thicker crusts than moist wounds during the inflammatory stage of healing. Collagen production is greater in the dermis of occluded wounds when compared to the dermis of air-exposed wounds. Furthermore, the dermis of superficial wounds exposed to the air is more fibroplastic, fibrotic, and scarred than the dermal component of a similar wound maintained in a moist environment. Epidermal cells migrate only over viable tissues as they require a blood and nutritional supply that is adequate to their energy needs. Because the migrating "tongue" of epithelium must burrow between any eschar (crest or scab) and the underlying tissue, the presence of this dry crust impedes wound healing. Thus, if the wound is kept moist and is protected from the external environment so that desiccation and crust formation is prevented, wound healing will occur at a more rapid pace.

Currently, the products available on the market to add moisture to the wound environment are either sterile, e.g., IntraSite™ Gel (commercially available from Smith & Nephew United, Inc., Quebec, Canada), or multi-component formulations containing, among other things, preservatives, e.g. Carrington Laboratories Dermal Wound Gel and Dressing™ (commercially available from Carrington Laboratories, Irvington, Tex.) and Biolex™ Wound Gel (commercially available from Catalina Biomedical Corporation, Duarte, Calif.).

IntraSite™ Gel is composed of water, propylene glycol, and a starch co-polymer. IntraSite™ Gel is sterilized using radiation prior to packing in foil packages, and therefore no preservatives are required. However, exposure of gels to radiation causes loss of viscosity due to rupture of cross links and depolymerization of polymer chain, all of which can possibly change color, odor, and clarity.

Other commercially available gels contain preservatives and do not require radiation sterilization. Preservatives, however, are cytotoxic, and additional ingredients are used to mitigate the effect.

Carrington's Dermal Wound Gel™ comprises three preservatives: sodium benzoate, potassium sorbate, and imidazolidinyl urea. The remaining components are purified water, povidone, panthenol, carbomer 940, triethanolamine, allantoin, glutamic acid, NaCl, methylparaben (also a preservative), acemannan hydrogel, citric acid and sodium metabisulfite. NaCl, allantoin, povidone, and panthenol most likely act to counter the cytotoxic effect of the preservatives.

Catalina's Biolex™ Wound Gel also comprises three preservatives: methyl/propyl paraben, K sorbate, and Diazolanal. Allantoin and panthenol are present and most likely act as cytotoxicity reducing agents.

The present invention is a non-cytotoxic wound hydrating gel which delivers water to a wound by means of an alginate based hydrating gel containing a preservative system comprised of potassium sorbate, boric acid, and DMDM hydantoin.

SUMMARY OF THE INVENTION

The present invention relates to a preserved, yet non-cytotoxic alginate based hydrating gel system for the purpose of treating wounds that need moisture. A hydrocolloid mixture of sodium carboxymethylcellulose and an alginate polymer blend impart sufficient viscosity to an aqueous solution to provide moisture to the wound. The mixture reduces the cytotoxicity of a combination of preservatives incorporated into the system. More specifically, the invention relates to a non-cytotoxic wound hydrating gel comprising a) a hydrocolloid mixture of carboxymethylcellulose and sodium/calcium alginate, and b) a preservative system. This invention further relates to methods of preparing and using the non-cytotoxic wound hydrating gel.

DETAILED DESCRIPTION OF THE INVENTION

This invention relates to a non-cytotoxic wound hydrating gel comprising a) a hydrocolloid mixture of sodium carboxymethylcellulose (CMC) and sodium/calcium alginate hydrocolloids, and optionally other hydrocolloids, and b) a preservative system. This invention further relates to methods of preparing and using said wound hydrating gel.

As used herein, the term "non-cytotoxic" refers to the characteristic of low cytotoxicity or no cytotoxicity (all or substantially all cells survive). The preferred sodium/calcium alginate hydrocolloid is a self gelling Na/Ca alginate having about 6–7% sodium minerals and about 2.5–3.5% calcium minerals (e.g., KELSET®, commercially available from Kelco, a division of Merck & Co., Inc.).

Preferably, CMC is present in an amount between about 0.1–1.0 wt. %, and Na/Ca alginate is present in an amount between about 0.2–2.00 wt. %. More preferably, CMC is present in an amount between about 0.2–0.8 wt. %, and Na/Ca alginate is present in an amount between about 0.5–1.5 wt. %. More preferably, CMC is present in an amount of about 0.6 wt. %, and Na/Ca alginate is present in an amount of about 1.5 wt. %.

Hydrocolloids which can optionally be used in additional to sodium/calcium alginate and CMC include Carbopol, including Carbopol 940, carrageenan, agar, and gelatin. The preservative system comprises dimethylol dimethylhydantoin (DMDM hydantoin) (commercially available from Lonza Chemical as Glydant 40-700, from McIntyre Chemical as Mackstat DM, and from Nipa Laboratories as Nipa Guard DMDMH), an antimicrobial agent and a mold and yeast inhibitor. Preferably, the antimicrobial agent is boric acid and the mold and yeast inhibitor is potassium sorbate. The relative weight percentages of these components is about 0.0.5–0.1% dimethylol dimethylhydantoin, 0.1–0.3% antimicrobial agent, and from 0 to about 1.0% mold and yeast inhibitor. The remaining portion of the composition is comprised of deionized water.

The pH ranges from about 5.5 to about 7.0, preferably about 6.5.

The composition of the present invention is prepared by adding deionized (DI) water to an appropriately sized vessel and initiating agitation, adding the potassium sorbate or other mold and yeast inhibitor, adding the dimethylol dimethylhydantoin, and adding the boric acid or other antimicrobial agent, adding the CMC slowly to the edge of the vortex and allowing the solution to mix for 60–90 minutes. The Na/Ca alginate powder is slowly added into the vortex of the solution and mixed into the solution for 60–90 minutes, or until product is uniform.

Once prepared, the wound hydrating gel is applied directly to the wound in order to "pack" the wound and provide a desirable healing environment, and may be conventionally delivered from a squeeze tube, a syringe or compressed air non-aerosol can, preferably by compressed air non-aerosol can.

The non-cytotoxic wound hydrating gel, which provides optimal environment for the moist wound healing process, is especially useful for management of pressure ulcers, stages I–IV, stasis ulcers, first and second degree burns, cuts, abrasions, skin tears and irritations of the skin.

In an exemplary application, a wound is cleansed with an appropriate non-cytotoxic solution such as SAF-Clens Chronic Wound Cleanser or Shur-Clens Skin Wound Cleansing Solution (both commercially available from Calgon Vestal Laboratories, St. Louis, Mo.) or with saline. A ⅛ to ¼ inch layer of the wound hydrating gel is applied to cover the entire wound. The layer is covered with an appropriate secondary dressing, such as gauze or other bandage. If gauze is used, it should be pre-moistened with saline or other appropriate noncytotoxic solutions. The gel is preferably changed daily or when the wound begins to dry.

The cytotoxicity of the present invention and those hydrating gels already on the market were determined using the Insert Cytotoxicity Assay described below.

Insert Cytotoxicity Assay—Part A: Gelatin Coating Millipore Inserts

Two hundred mls of sterile distilled water were added to a 300 ml beaker and heated until boiling. One hundred mgs of gelatin was then added and the solution mixed until the gelatin was completely dissolved. One ml of the still hot gelatin solution was then added to each Millipore insert sitting upright in an individual well of a 6 well plate. The plates are then placed in a 50° C. oven with the lids slightly ajar overnight or until dry. The gelatin coated inserts are then stored in the refrigerator at 4° C. for use in Part B.

Insert Cytotoxicity Assay—Part B: Millipore Inserts Direct Contact Test

From a confluent flask of commercially available L929 mouse fibroblast cells, media was aspirated from the monolayer and the monolayer washed with 10 ml of modified Hanks Balanced Salts Solution (without calcium and magnesium with phenol red ("HBSS", Whittaker Bioproducts)). The media was again aspirated and 10 ml of Trypsin was added. Following incubation for 10 minutes at 37° C., the monolayer was gently dislodged and 10 ml of growth media (10X EMEM (10%), 200 mm Glutamine (1%), Fetal Bovine Serum (5%), Omni Serum (5%), 7.5% $NaHCO_3$ (2%), Sterile distilled water (77%), commercially available from Whittaker Bioproducts) was added to quench the Trypsin. After mixing, the solution was aliquoted into a large 50 milliliter centrifuge tube and centrifuged at 1000 rpm for 10 minutes with no brake. The supernatant was aspirated and the cells resuspended with a vortex in 2–10 mls of growth media, depending on the size of the cell pellet. The exact amount of media added is not critical. The cells are then counted via the cell counting procedure described below.

Cell counting procedure: Suspend the cells as completely and evenly as possible. In a 13×100 mm plastic tube, combine 0.5 ml Trypan blue stain, 0.3 ml HBSS, and 0.2 ml cell suspension. Allow to stand at room temperature for 10 minutes. Fill both chambers of a Hemocytometer with the cell/dye suspension as follows: Place the coverslip on the clean, dry hemocytometer and use a pasteur pipet to fill the chambers by capillary action. This is best done by touching the edge of the coverslip with the pasteur pipet. Place the hemocytometer under a microscope and focus until a gridwork is seen. The gridwork is the "chamber" for one side. The area that is ⅕th of the chamber is referred to as a "square." Count the colorless cells (that have excluded the blue dye) in the squares indicated below, 5 squares per side of the hemocytometer. Calculate the average number of cells per square, multiply by the dilution factor (5) and multiply by $10^4$. This will give the number of cells per milliliter.

After counting, the cells were diluted in growth media containing antibiotics (Penn/Strep fungizone, available from Whittaker Bioproducts, 1 ml per 100 ml of growth media) to a final concentration of $9 \times 10^4$ cells/ml. One ml of this cell suspension was then added to each gelatin coated Millipore insert aseptically transferred from the 6 well plate in Part A to a clean 6 well plate wherein, to each well, 6 mls of standard growth media was added outside of the insert and 3 mls to the inside of the insert. The plates were then incubated for 6 days at 37° C., 5%, $CO_2$.

2.5 mls or 2.5 gms of each sample of gel to be tested were distributed into a clean 6 well plate, 1 sample per well. 0.0050 gms of sodium lauryl sulfate were also added to a well containing a noncytotoxic control gel to make 0.10% SLS gel.

The plates being incubated were removed from the incubator. The inserts were aseptically removed from the media and one was placed in a well on top of each sample of gel to be tested. 3 mls of growth media were added to the top of each insert, and the plates containing the gel samples were then incubated at 37° C., 5% $CO_2$, for 4 hours.

After incubation, the inserts were aseptically removed from the samples and placed in a clean 6 well plate. 2 mls of a standard fluorescein diacetate solution (prepared by dissolving 0.01 grams of powdered Fluorescein diacetate dye in 2 ml of acetone, then diluting the stock solution 1:250 in phosphate buffered saline) were added on top of the insert, and 2 mls outside of the insert. The inserts were then refrigerated at 4° C. for 20 minutes and finally read under an inverted fluorescent scope. Plates were viewed with bright field and fluorescent settings. Several fields were viewed per insert, and an average percentage of fluorescent cells (as compared to the number of cells visible under brightfield) was recorded.

A summary of the results of the assay comparing the present invention with the hydrating gels already on the market is given in the table following the examples. The following examples are illustrative only and are not intended to limit or restrict the present invention in any manner.

EXAMPLE 1

| ITEM | WEIGHT % | WEIGHT (gms) |
|---|---|---|
| DI Water | 97.59 | 975.9 |
| K Sorbate | 0.2 | 2.0 |
| DMDM Hydantoin | 0.1 | 1.0 |
| Boric Acid | — | — |
| CMC | 0.6 | 6.0 |
| KELSET ® | 1.5 | 15.0 | pH: 6.5

Three aliquots of this batch were then assayed as described above.

EXAMPLE 2

| ITEM | WEIGHT % | WEIGHT (gms) |
|---|---|---|
| DI Water | 97.55 | 975.5 |
| K Sorbate | 0.2 | 2.0 |
| DMDM Hydantoin | 0.1 | 1.0 |
| Boric Acid | — | — |
| CMC | 0.6 | 6.0 |
| KELSET ® | 1.5 | 15.0 | pH: 6.0

Three aliquots of this batch were then assayed as described above.

EXAMPLE 3

| ITEM | WEIGHT % | WEIGHT (gms) |
|---|---|---|
| DI Water | 97.6 | 976.0 |
| K Sorbate | 0.2 | 2.0 |
| DMDM Hydantoin | 0.1 | 1.0 |
| Boric Acid | — | — |
| CMC | 0.6 | 6.0 |
| KELSET ® | 1.5 | 15.0 | pH: 7.0 (unadjusted)

Three aliquots of this batch were then assayed as described above.

EXAMPLE 4

| ITEM | WEIGHT % | WEIGHT (gms) |
|---|---|---|
| DI Water | 97.1 | 971.0 |
| K Sorbate | 0.2 | 2.0 |
| DMDM Hydantoin | 0.1 | 1.0 |
| Boric Acid | 0.5 | 5.0 |
| CMC | 0.6 | 6.0 |
| KELSET ® | 1.5 | 15.0 | pH: 7.0

Three aliquots of this batch were then assayed as described above.

EXAMPLE 5

| ITEM | WEIGHT % | WEIGHT (gms) |
|---|---|---|
| DI Water | 97.1 | 971.1 |
| K Sorbate | 0.2 | 2.0 |
| DMDM Hydantoin | 0.1 | 1.0 |
| Boric Acid | 0.5 | 5.0 |
| CMC | 0.6 | 6.0 |
| KELSET ® | 1.5 | 15.0 | pH: 6.5

Three aliquots of this batch were then assayed as described above.

EXAMPLE 6

| ITEM | WEIGHT % | WEIGHT (gms) |
|---|---|---|
| DI Water | 97.1 | 971.0 |
| K Sorbate | 0.2 | 2.0 |
| DMDM Hydantoin | 0.1 | 1.0 |
| Boric Acid | 0.5 | 5.0 |
| CMC | 0.6 | 6.0 |
| KELSET ® | 1.5 | 15.0 | pH: 6.0

Three aliquots of this batch were then assayed as described above.

EXAMPLE 7

| ITEM | WEIGHT % | WEIGHT (gms) |
|---|---|---|
| DI Water | 87.1 | 871.0 |
| K Sorbate | 0.2 | 2.0 |
| DMDM Hydantoin | 0.1 | 1.0 |
| Boric Acid | 0.5 | 5.0 |
| CMC | 0.6 | 6.0 |
| KELSET ® | 1.5 | 15.0 |
| Propylene glycol | 10.0 | 100.0 |

EXAMPLE 8

| ITEM | WEIGHT % | WEIGHT (gms) |
|---|---|---|
| DI Water | 87.1 | 871.0 |
| K Sorbate | 0.2 | 2.0 |
| DMDM Hydantoin | 0.1 | 1.0 |
| Boric Acid | 0.5 | 5.0 |
| CMC | 0.6 | 6.0 |
| KELSET ® | 1.5 | 15.0 |
| Glycerin | 10.0 | 100.0 |

EXAMPLE 9

| ITEM | WEIGHT % | WEIGHT (gms) |
|---|---|---|
| DI Water | 87.46 | 874.6 |
| K Sorbate | 0.2 | 2.0 |
| DMDM Hydantoin | 0.1 | 1.0 |
| Boric Acid | 0.5 | 5.0 |
| CMC | 0.04 | 0.4 |
| KELSET ® | 0.2 | 2.0 |
| Carbopol 940 | 0.75 | 7.5 |
| Propylene glycol | 10.0 | 100.0 |
| Triethanolamine | 0.75 | 7.5 |

EXAMPLE 10

| ITEM | WEIGHT % | WEIGHT (gms) |
|---|---|---|
| DI Water | 87.0 | 870.0 |
| K Sorbate | 0.2 | 2.0 |
| DMDM Hydantoin | 0.1 | 1.0 |
| Boric Acid | 0.5 | 5.0 |
| CMC | 0.1 | 1.0 |
| KELSET ® | 0.5 | 5.0 |
| Carbopol 940 | 0.5 | 5.0 |
| Propylene glycol | 10.0 | 100.0 |
| Triethanolamine | 0.5 | 5.0 |

EXAMPLE 11

| ITEM | WEIGHT % | WEIGHT (gms) |
| --- | --- | --- |
| DI Water | 97.25 | 972.5 |
| K Sorbate | 0.2 | 2.0 |
| DMDM Hydantoin | 0.1 | 1.0 |
| Boric Acid | 0.5 | 5.0 |
| CMC | 0.2 | 2.0 |
| KELSET ® | 1.75 | 17.5 |

EXAMPLE 12

| ITEM | WEIGHT % | WEIGHT (gms) |
| --- | --- | --- |
| DI Water | 97.9 | 979.0 |
| K Sorbate | 0.2 | 2.0 |
| DMDM Hydantoin | 0.1 | 1.0 |
| Boric Acid | 0.5 | 5.0 |
| CMC | 0.8 | 8.0 |
| KELSET ® | 0.5 | 5.0 |

TABLE

L929 mouse fibroblast cell viability ≧

| Product | % viable cells | | |
| --- | --- | --- | --- |
| | start | end | % loss |
| control (saline, no gel) | 100 | 95 | 5 |
| Carrington Laboratories Dermal Wound Gel and Dressing ™ | 80 | 72 | 8 |
| Carrington Laboratories Dermal Wound Gel and Dressing ™ | 100 | 90 | 10 |
| Carrington Laboratories Dermal Wound Gel and Dressing ™ | 100 | 100 | 0 |
| Biolex | 100 | 10 | 90 |
| " | 80 | 8 | 72 |
| 1.5% Na./Ca alginate | 100 | 90 | 10 |
| " | 100 | 90 | 10 |
| IntraSite ™ Gel | 100 | 95 | 5 |
| " | 100 | 100 | 0 |
| 1.5% Na./Ca alginate with sodium lauryl sulfate | 100 | 0 | 100 |
| KELSET ® with sodium lauryl sulfate | 100 | 0 | 100 |
| KELSET ® | 100 | 80 | 20 |
| Example 1 | 100 | 85 | 15 |
| Example 2 | 100 | 93.3 | 6.7 |
| Example 3 | 100 | 95 | 5 |
| Example 4 | 100 | 96.7 | 3.3 |
| Example 5 | 100 | 90 | 10 |
| Example 6 | 100 | 93.3 | 6.7 |

For examples 1–6, % viable cells at end is represented as an average of three evaluated samples.

These tables clearly show that the non-cytotoxic wound hydrating gel of the present invention has an equivalent or superior toxicity profile as compared to the products currently available on the market. Furthermore, unlike the prior art, this low cytotoxicity is achieved without the addition of other ingredients to counter the toxicity of the preservatives located therein.

What is claimed is:

1. A non-cytotoxic wound hydrating gel consisting essentially of:

a. a hydrocolloid system of sodium/calcium alginate and sodium carboxymethylcellulose, and b. a preservative system of dimethylol dimethylhydantoin, an antimicrobial agent and a mold and yeast inhibitor.

2. The non-cytotoxic wound hydrating gel of claim 1 wherein the sodium/calcium alginate is selected from the group consisting of sodium/calcium alginates having about 6–7% sodium minerals and about 2.5–3.5% calcium minerals.

3. The non-cytotoxic wound hydrating gel of claim 1 wherein sodium carboxymethylcellulose is present in an amount of about 0.1–1.0 wt. %, and sodium/calcium alginate is present in an amount of about 0.2–2.00 wt. %.

4. The non-cytotoxic wound hydrating gel of claim 3 wherein sodium carboxymethylcellulose is present in an amount of about 0.2–0.8 wt. %, and sodium/calcium alginate is present in an amount of about 0.5–1.5 wt. %.

5. The non-cytotoxic wound hydrating gel of claim 4 wherein sodium carboxymethylcellulose is present in an amount of about 0.6 wt. %, and sodium/calcium alginate is present in an amount of about 1.5 wt. %.

6. The non-cytotoxic wound hydrating gel of claim 1 wherein:

a. the antimicrobial agent is boric acid, and b. the mold and yeast inhibitor is potassium sorbate.

7. The non-cytotoxic wound hydrating gel of claim 6 wherein the relative weight percentages of the non-water components are:

| | |
| --- | --- |
| Sodium/Calcium Alginate | about 1.5% |
| Dimethylol Dimethylhydantoin | about 0.1% |
| Potassium Sorbate | about 0.2% |
| Boric Acid | about 0.5% |
| Sodium Carboxymethylcellulose | about 0.6%. |

8. A process for preparing the non-cytotoxic wound hydrating gel of claim 1 comprising the steps of:

a. dissolving, with agitation, all components of the preservative system in deionized water to form a solution and thereafter maintaining the agitation so that a vortex is present;

b. adding sodium carboxymethylcellulose to the edge of the vortex and allowing the solution to mix for 60–90 minutes;

c. adding sodium/calcium alginate powder into the vortex of the solution; and d. mixing the solution until a uniform product is obtained.

9. A method of providing a moist wound environment to facilitate the healing process of a wound comprising the step of applying directly to the wound a non-cytotoxic hydrating gel of claim 1.

10. A method of providing a moist wound environment to facilitate the healing process of a wound comprising the step of applying directly to the wound a non-cytotoxic hydrating gel of claim 2.

11. A method of providing a moist wound environment to facilitate the healing process of a wound comprising the step of applying directly to the wound a non-cytotoxic hydrating gel of claim 3.

12. A method of providing a moist wound environment to facilitate the healing process of a wound comprising the step of applying directly to the wound a non-cytotoxic hydrating gel of claim 4.

13. A method of providing a moist wound environment to facilitate the healing process of a wound comprising the step of applying directly to the wound a non-cytotoxic hydrating gel of claim 5.

14. A method of providing a moist wound environment to facilitate the healing process of a wound comprising the step of applying directly to the wound a non-cytotoxic hydrating gel of claim 6.

15. A method of providing a moist wound environment to facilitate the healing process of a wound comprising the step of applying directly to the wound a non-cytotoxic hydrating gel of claim 7.

16. The non-cytotoxic wound hydrating gel of claim 6 wherein the relative weight percentages of the non-water components are:

| | |
|---|---|
| Sodium/Calcium Alginate | about 0.2% |
| Dimethylol Dimethylhydantoin | about 0.1% |
| Potassium Sorbate | about 0.2% |
| Boric Acid | about 0.5% |
| Sodium Carboxymethylcellulose | about 0.04%. |

\* \* \* \* \*